United States Patent
Ohtake et al.

(10) Patent No.: US 9,072,783 B2
(45) Date of Patent: *Jul. 7, 2015

(54) HIGHLY DISPERSIBLE POWDERS, COMPOSITIONS AND METHODS FOR PREPARATION

(75) Inventors: Satoshi Ohtake, Chesterfield, MO (US); Atul Saxena, Milpitas, CA (US); Vu Truong-Le, Campbell, CA (US)

(73) Assignee: Aridis Pharmaceuticals, San Jose, CA (US)

( * ) Notice: Subject to any disclaimer, the term of this patent is extended or adjusted under 35 U.S.C. 154(b) by 243 days.

This patent is subject to a terminal disclaimer.

(21) Appl. No.: 13/988,248

(22) PCT Filed: Nov. 18, 2010

(86) PCT No.: PCT/US2010/057234
§ 371 (c)(1),
(2), (4) Date: May 17, 2013

(87) PCT Pub. No.: WO2011/063126
PCT Pub. Date: May 26, 2011

(65) Prior Publication Data
US 2013/0302425 A1    Nov. 14, 2013

Related U.S. Application Data

(60) Provisional application No. 61/262,222, filed on Nov. 18, 2009.

(51) Int. Cl.
A61K 47/18    (2006.01)
A61K 9/16     (2006.01)
A61K 33/24    (2006.01)

(52) U.S. Cl.
CPC .............. *A61K 47/183* (2013.01); *A61K 9/1617* (2013.01); *A61K 33/24* (2013.01)

(58) Field of Classification Search
None
See application file for complete search history.

(56) References Cited

U.S. PATENT DOCUMENTS

| | | | |
|---|---|---|---|
| 7,078,509 B2 | 7/2006 | Baum et al. | |
| 2003/0186894 A1 | 10/2003 | Kuo et al. | |
| 2004/0052733 A1* | 3/2004 | Staniforth et al. | 424/46 |
| 2009/0123562 A1* | 5/2009 | Bender et al. | 424/617 |
| 2009/0247567 A1 | 10/2009 | Do et al. | |

OTHER PUBLICATIONS

International Search Report for PCT/US2010/057234, dated Jan. 27, 2011.

* cited by examiner

*Primary Examiner* — David J Blanchard
*Assistant Examiner* — Daniel F Coughlin
(74) *Attorney, Agent, or Firm* — Kilpatrick Townsend Stockton LLP

(57) ABSTRACT

A method for the selection of pharmaceutically acceptable excipients that allow for the production of highly dispersible powders produced by spray drying.

16 Claims, 6 Drawing Sheets

HIGHLY DISPERSIBLE POWDERS, COMPOSITIONS AND METHODS FOR PREPARATION

CROSS-REFERENCES TO RELATED APPLICATIONS

This application is the U.S. National Stage entry under §371 of International Application No. PCT/US2010/057234, filed Nov. 18, 2010, which claims priority from U.S. Provisional 61/262,222 filed Nov. 18, 2009. The International Application and U.S. provisional application are each incorporated herein by reference.

STATEMENT AS TO RIGHTS TO INVENTIONS MADE UNDER FEDERALLY SPONSORED RESEARCH OR DEVELOPMENT

Certain aspects of the invention disclosed herein were made with United States government support under NIH NIAID SBIR 1 R43AI081400-01. The United States government may have certain rights in the invention.

FIELD OF THE INVENTION

The invention is a method to engineer highly dispersible powders. The hydropathy index and the water-to-vapor transfer free energy of pharmaceutically acceptable excipients are used to guide the selection of excipients that improve the aerosol properties of a spray dried powder.

BACKGROUND OF THE INVENTION

Pharmaceutically acceptable excipients can be classified according to their hydrophilicy/hydrophobicity index and the transfer (Gibbs) free energy associated with the transition of excipients from one phase to another, such as from water to vapor (i.e. delta $G_{water-vapor}$). Kyte and Doolittle described the hydrophobicity index as a scale in which the tendency of the molecule to segregate into either the polar or non-polar phases is rank ordered (Kyte and Doolittle (1982) *J. Mol. Biol.* 157, 105-132). They have reported on the hydrophobicity of the 20 amino acids based on their relative abundance in various structural segments of proteins (hydropathy index). Based on these studies, the amino acids were arranged in the order of increasing hydrophobicity, e.g. higher frequency with which the amino acids are found in the core of the proteins. In a similar manner, other molecules such as peptides, proteins, and polymers can be classified according to the hydropathy index.

The current invention uses the hydropathy index or transfer (Gibbs) free energy as a guide in selecting the molecules that can be added to a solution to engineer the formation of particles with the desired characteristics (i.e. dispersibility, fine particle fraction, etc.).

BRIEF SUMMARY OF THE INVENTION

The methods of the present invention include the use of the hydropathy index and transfer (Gibbs) free energy of pharmaceutically acceptable excipients as a guide in selecting components that allow for the production of highly dispersible powders by spray drying.

Several amino acids were chosen, according to the hydropathy index or to the transfer (Gibbs) free energy (Kyte and Doolittle (1982) *J. Mol. Biol.* 157, 105-132), and incorporated into a solution containing gallium nitrate and sodium citrate. The incorporation of amino acids with a high hydropathy index, such as leucine, resulted in spray dried powders with lower mean mass aerodynamic diameter (MMAD) and higher fine particle distribution ($FPD_{<4.7\ \mu m}$) compared to those of powders produced in the absence of amino acids. Other molecules, such as proteins, polymers, and surfactants, were also examined.

The present invention provides a formulation, composition, and method, wherein the hydropathy index scale is employed as a guide to select pharmaceutically acceptable excipients to engineer highly dispersible powders. Also, what is provided is the above formulation, composition, and method, wherein the pharmaceutically acceptable excipient is an amino acid selected from leucine, isoleucine, valine, alanine, phenylalanine, cysteine, methionine, threonine, serine, tryptophan, tyrosine, lysine, glutamine, asparagine, glutamic acid, histidine, aspartic acid, arginine, glycine, proline, their derivatives, and mixtures thereof. What the invention also embraces, is the above formulation, composition, and method wherein the pharmaceutically acceptable excipient is leucine, or wherein the pharmaceutically acceptable excipient is isoleucine, or whereby the pharmaceutically acceptable excipient is a peptide found to be either amphiphilic or hydrophobic according to the hydropathy index scale, or whereby the pharmaceutically acceptable excipient is found to be either amphiphilic or hydrophobic.

In yet another aspect, the present invention encompasses the above formulation, composition, and method, wherein the pharmaceutically acceptable excipient is a polymer found to be either amphiphilic or hydrophobic according to the hydropathy index scale, or wherein the pharmaceutically acceptable excipient is a surfactant found to be either amphiphilic or hydrophobic according to the hydropathy index scale, or whereby the powder is produced by spray drying. Moreover, what is provided by the invention is a formulation, composition, and method wherein the transfer (Gibbs) free energy delta $G_{water-vapor}$ of the pharmaceutically acceptable excipient is employed as a guide to select components to engineer highly dispersible powders. In another aspect, the invention provides the above formulation, composition, and method, wherein the pharmaceutically acceptable excipient is an amino acid selected from leucine, isoleucine, valine, alanine, phenylalanine, cysteine, methionine, threonine, serine, tryptophan, tyrosine, lysine, glutamine, asparagine, glutamic acid, histidine, aspartic acid, arginine, glycine, proline, their derivatives, and mixtures thereof, and the above formulation, composition, and method, wherein the pharmaceutically acceptable excipient is leucine, as well as the above formulation, composition, and method, wherein the pharmaceutically acceptable excipient is isoleucine. Additionally, what is provided is the above formulation, composition, and method, wherein the pharmaceutically acceptable excipient is a peptide found to be either amphiphilic or hydrophobic according to the hydropathy index scale, as well as the above composition, formulation, and method, wherein the pharmaceutically acceptable excipient is a protein found to be either amphiphilic or hydrophobic according to the hydropathy index scale, or wherein the pharmaceutically acceptable excipient is a polymer found to be either amphiphilic or hydrophobic according to the hydropathy index scale, or wherein the pharmaceutically acceptable excipient is a surfactant found to be either amphiphilic or hydrophobic according to the hydropathy index scale, or wherein the powder is produced by spray drying.

The present invention also provides a pharmaceutically acceptable dispersible powder, comprising gallium and a hydrophobic amino acid that is more hydrophobic than alanine, according to the Kyte-Doolittle index, wherein the mass of the amino acid is 15%-25% of the mass of the powder, and wherein the fine particle distribution (FPD) of the powder that is under 3.3 microns is greater than 30%, or wherein the mass median aerodynamic diameter (MMAD) of the powder is under 10 microns.

In some embodiments, the excipient is selected from the group consisting of a lipid, cholesterol, triglyceride, lipoprotein, glycolipid, alkane, oil, and fat. In some embodiments, the excipient is an amino acid. In some embodiments, the mass of the excipient (e.g., amino acid) is at least 20.5% the mass of the powder and 22% or less than the mass of the powder. In some embodiments, the mass of the excipient (e.g., amino acid) is about 21% of the mass of the powder. In some embodiments, the gallium is formulated as gallium citrate or gallium nitrate. In some embodiments, the amino acid is leucine. In some embodiments, the amino acid is selected from the group consisting of isoleucine, valine, phenylalanine, cysteine, and methionine. In some embodiments, the powder is made by a method comprising spray freeze-drying, fluidized bed drying, supercritical fluid assisted drying, or spray coating.

The present invention also provides for a pharmaceutically acceptable dispersible powder comprising a hydrophobic amino acid, other than leucine, that is more hydrophobic than alanine, according to the Kyte-Doolittle index, wherein the mass of the amino acid is 15%-25% of the mass of the powder, and wherein the fine particle distribution (FPD) of the powder that is under 3.3 microns is greater than 30%, or wherein the mass median aerodynamic diameter (MMAD) of the powder is under 10 microns.

In some embodiments, the excipient is selected from the group consisting of a lipid, cholesterol, triglyceride, lipoprotein, glycolipid, alkane, oil, and fat. In some embodiments, the excipient is an amino acid. In some embodiments, the powder further comprises a pharmaceutically-active compound. In some embodiments, the pharmaceutically-active compound is gallium. In some embodiments, the pharmaceutically-active compound is gallium citrate or gallium nitrate. In some embodiments, the mass of the excipient (e.g., amino acid) is at least 20.5% the mass of the powder and 22% or less than the mass of the powder. In some embodiments, the mass of the excipient (e.g., amino acid) is about 21% of the mass of the powder. In some embodiments, the amino acid is selected from the group consisting of isoleucine, valine, phenylalanine, cysteine, and methionine. In some embodiments, the powder is made by a method comprising spray freeze-drying, fluidized bed drying, supercritical fluid assisted drying, or spray coating.

The present invention also provides a pharmaceutically acceptable dispersible powder comprising leucine, wherein the mass of the leucine is at least 20.5% the mass of the powder and 22% or less than the mass of the powder, and wherein the fine particle distribution (FPD) of the powder that is under 3.3 microns is greater than 30%, or wherein the mass median aerodynamic diameter (MMAD) of the powder is under 10 microns.

In some embodiments, the mass of the amino acid is about 21% of the mass of the powder. In some embodiments, the powder further comprises a pharmaceutically-active compound. In some embodiments, the pharmaceutically-active compound is gallium. In some embodiments, the pharmaceutically-active compound is gallium citrate or gallium nitrate. In some embodiments, the powder is made by a method comprising spray freeze-drying, fluidized bed drying, supercritical fluid assisted drying, or spray coating.

The invention also provides for methods for formulating a pharmaceutically acceptable dispersible powder for use as an aerosol, the method comprising the steps of:

(a) selecting a hydropathy index that comprises at least two different excipients;

(b) selecting an excipient from the hydropathy index, wherein the selected excipient has a greater hydropathy than at least one of the other excipients of the index;

(c) selecting a drug; and (d) formulating the pharmaceutically acceptable dispersible powder by the selected excipient and the selected drug; wherein the mass of the excipient is 15%-25% of the mass of the powder, and wherein the fine particle distribution (FPD) of the powder that is under 3.3 microns is greater than 30%, or wherein the mass median aerodynamic diameter (MMAD) of the powder is under 10 microns.

In some embodiments, the fine particle distribution (FPD) of the powder that is under 3.3 microns is greater than about 37%. In some embodiments, the fine particle distribution (FPD) of the powder that is under 3.3 microns is greater than about 43%. In some embodiments, the mass of the excipient is 15%-30% of the mass of the powder. In some embodiments, the wherein the mass of the excipient is about 21% of the mass of the powder. In some embodiments, the excipient comprises an amino acid. In some embodiments, the amino acid is selected from the group consisting of leucine, isoleucine, valine, phenylalanine, cysteine, and methionine. In some embodiments, the excipient is selected from the group consisting of a phospholipid, oligopeptide, and protein. In some embodiments, the excipient comprises a lipid having the same structure as a lipid of mammalian lung fluids. In some embodiments, the hydropathy index is the Kyte-Doolittle index. In some embodiments, the hydropathy index is a lipophilicity index. In some embodiments, the hydropathy index is a transfer free energy (ΔGwater-vapor) index.

DEFINITIONS

Unless otherwise defined herein or below in the remainder of the specification, all technical and scientific terms used herein have meanings commonly understood by those of ordinary skill in the art to which the present invention belongs.

Before describing the present invention in detail, it is to be understood that this invention is not limited to particular devices or biological systems, which can, of course, vary. It is also to be understood that the terminology used herein is for the purpose of describing particular embodiments only, and is not intended to be limiting. As used in this specification and the appended claims, the singular forms “a”, “an” and “the” include plural referents unless the content clearly dictates otherwise. Thus, for example, reference to “a component” can include a combination of two or more components; reference to “a buffer” can include mixtures of buffers, and the like.

Although many methods and materials similar, modified, or equivalent to those described herein can be used in the practice of the present invention without undue experimentation, the preferred materials and methods are described herein. In describing and claiming the present invention, the following terminology will be used in accordance with the definitions set out below.

An “amino acid” refers to any monomer unit that can be incorporated into a peptide, polypeptide, or protein. As used herein, the term “amino acid” includes the following twenty natural or genetically encoded alpha-amino acids: alanine (Ala or A), arginine (Arg or R), asparagine (Asn or N), aspartic acid (Asp or D), cysteine (Cys or C), glutamine (Gln or Q), glutamic acid (Glu or E), glycine (Gly or G), histidine (His or H), isoleucine (Ile or I), leucine (Leu or L), lysine (Lys or K), methionine (Met or M), phenylalanine (Phe or F), proline (Pro or P), serine (Ser or S), threonine (Thr or T), tryptophan (Trp or W), tyrosine (Tyr or Y), and valine (Val or V). The structures of these twenty natural amino acids are shown in, e.g., Stryer et al., Biochemistry, 5$^{th}$ ed., Freeman and Company (2002), which is incorporated by reference. Additional amino acids, such as selenocysteine and pyrrolysine, can also be genetically coded for (Stadtman (1996) "Selenocysteine," Annu Rev Biochem. 65:83-100 and Ibba et al. (2002) "Genetic code: introducing pyrrolysine," Curr Biol. 12(13):R464-R466, which are both incorporated by reference). The term "amino acid" also includes unnatural amino acids, modified amino acids (e.g., having modified side chains and/or backbones), and amino acid analogs. See, e.g., Zhang et al. (2004) "Selective incorporation of 5-hydroxytryptophan into proteins in mammalian cells," Proc. Natl. Acad. Sci. U.S.A. 101 (24):8882-8887, Anderson et al. (2004) "An expanded genetic code with a functional quadruplet codon" Proc. Natl. Acad. Sci. U.S.A. 101(20):7566-7571, Ikeda et al. (2003) "Synthesis of a novel histidine analogue and its efficient incorporation into a protein in vivo," Protein Eng. Des. Sel. 16(9):699-706, Chin et al. (2003) "An Expanded Eukaryotic Genetic Code," Science 301 (5635):964-967, James et al. (2001) "Kinetic characterization of ribonuclease S mutants containing photoisomerizable phenylazophenylalanine residues," Protein Eng. Des. Sel. 14(12):983-991, Kohrer et al. (2001) "Import of amber and ochre suppressor tRNAs into mammalian cells: A general approach to site-specific insertion of amino acid analogues into proteins," Proc. Natl. Acad. Sci. U.S.A. 98(25):14310-14315, Bacher et al. (2001) "Selection and Characterization of Escherichia coli Variants Capable of Growth on an Otherwise Toxic Tryptophan Analogue," J. Bacteriol. 183(18):5414-5425, Hamano-Takaku et al. (2000) "A Mutant Escherichia coli Tyrosyl-tRNA Synthetase Utilizes the Unnatural Amino Acid Azatyrosine More Efficiently than Tyrosine," J. Biol. Chem. 275(51):40324-40328, and Budisa et al. (2001) "Proteins with {beta}-(thienopyrrolyl)alanines as alternative chromophores and pharmaceutically active amino acids," Protein Sci. 10(7): 1281-1292, which are each incorporated by reference.

The term "about", as used herein, indicates the value of a given quantity can include quantities ranging within 10% of the stated value, or optionally within 5% of the value, or in some embodiments within 1% of the value.

As used herein, the terms "solution" and "suspension" and "liquid formulation" are used interchangeably.

"Pharmaceutically acceptable" refers to those active agents, salts, and excipients which are, within the scope of sound medical judgment, suitable for use in contact with the tissues or humans and lower animals without undue toxicity, irritation, allergic response and the like, commensurate with a reasonable benefit/risk ratio, and effective for their intended use.

DETAILED DESCRIPTION OF THE INVENTION

Figure 1:
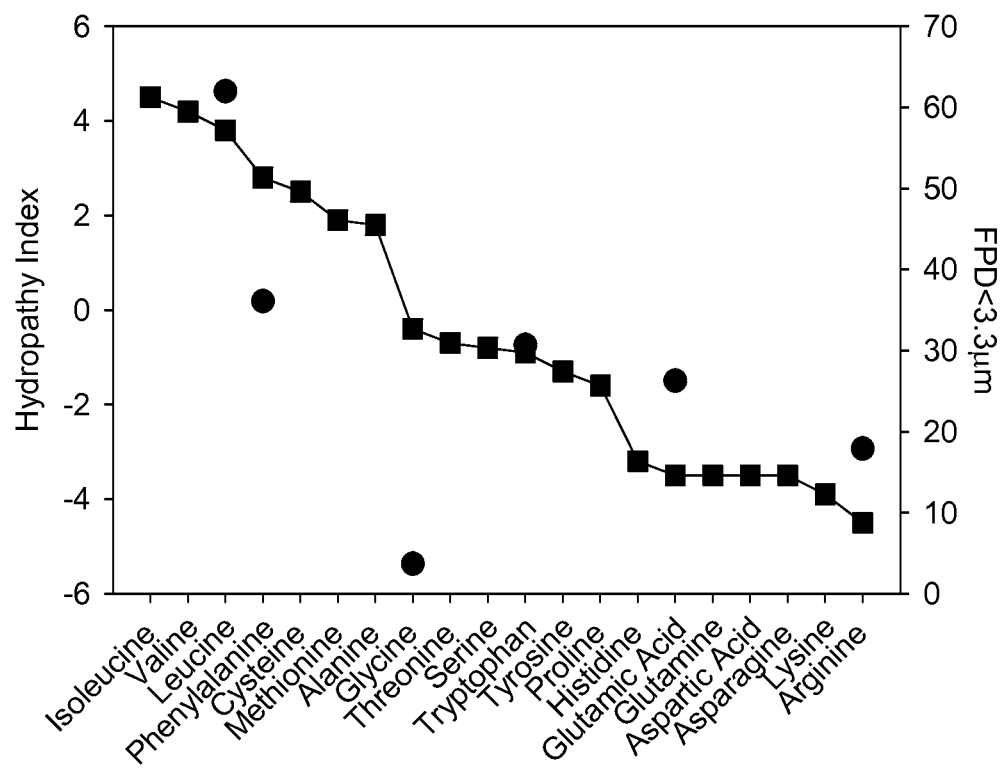
FIG. 1 shows the correlation between the hydropathy index (■) of the amino acids to the $FPD_{<3.3 \mu m}$ (●) of the spray dried powders containing gallium-citrate.

The present invention is directed to methods of engineering highly dispersible powders through the use of the hydropathy index and/or the transfer (Gibbs) free energy (i.e. delta $G_{water-vapor}$) of pharmaceutically acceptable excipients as a guide in selecting the appropriate components. Various indices can be used for designing and formulating dispersible powders of the present invention, including, but not limited to, a hydropathy index, hydropathy plot, lipophilicity index, hydrophobicity index, and the like. As demonstrated in the Examples, use of a hydrophobic excipient that is more hydrophobic that alanine based on a hydropathy index or Gibbs free energy index allows one to design and formulate dispersible powders that are generally superior in the quantity of small-sized particles than would otherwise be possible. Once the excipient has been identified, one can formulate a powder according to any of the optimal concentrations of excipient as described herein and produce the powder, for example by the production methods described herein.

Moreover, the Examples demonstrate for the first that surprisingly the percentage of particles less than 4.7 mm increases dramatically with formulation of powders with amino acids of a concentration between 15-25% of the mass of the powder, with particularly surprising yield of small particles when the amino acid concentration is about 21%, e.g., between 20.5-22% of the mass of the powder.

Indices for use in the invention include but are not limited to the hydropathy index of Kyte and Doolittle (Kyte J, Doolittle R F (1982) A simple method for displaying the hydropathic character of a protein. J. Mol. Biol. 157:105-132), the hydropathy, or lipophilicity, index of Liu, et al. (2008) Lipophilicity measurement of drugs by reversed phase HPLC over wide pH range using an alkaline-resistant silica-based stationary phase, XBridge™ Shield $RP_{18}$. Chem. Pharm. Bull. (Tokyo) 56:1417-1422, of Markuszewski, et al. (2004) High-throughput evaluation of lipophilicity and acidity by new gradient HPLC methods. Comb. Chem. High Throughput. Screen. 7:281-289. Further guidance comes from, Avdeef (2001) Physicochemical profiling (solubility, permeability and charge state) Curr. Top. Med. Chem. 1:277-351. Guidance for relative hydrophilicity of various surfactants and emulsifiers comes from, for example, Das, et al. (2005) Head-group size or hydrophilicity of surfactants. Chemistry 11:4881-4889, and from, Noiret, et al. (1999) Polyglyceryl amines as surfactants: symmetrical polyglyceryl amines and aqueous solution properties. J. Surfactants Detergents 2:349-355, Chen and Wang (1992) Synthesis and surface activity of self-sequestering surfactants. JAOCS 69:60-63, U.S. Pat. No. 6,462,000 issued to Kupfer. Additional guidance comes from scales that disclose hydrophilic-lipophilic-balance (HLB). See, e.g., Waggoner and Fincher (1971), Influence of HLB values of surfactants on ephedrine release from emulsified liquid systems. J. Pharm. Sci. 60:1830-1835, and U.S. Pat. No. 4,786,502 issued to Capura.

In some aspects, the highly dispersible powder of the present invention does not comprise a cytokine, does not comprises a cytokine receptor, does not comprise dileucine or derivatives thereof, does not comprise trileucine or derivatives thereof. In yet another aspect, what is encompassed by the invention are particles that have a surface that is rough or characterized by wrinkles, particles that are generally spherical, and particles that are generally spherical that have a surface that is rough or characterized by wrinkles. In other aspects, the highly dispersible powder of the present invention comprises an excipient that is approved by the U.S. Food and Drug Administration (FDA) for human use. In yet other aspects, the highly dispersible powder of the present invention does not comprise an excipient that is not approved by the FDA for human use.

Without intending any limitation, the use of human serum albumin in the present experiments can serve as a surrogate for a pharmaceutical protein, such as insulin, alpha 1 antitrypsin, some vaccines, recombinant DNAs, and the like, in the context of particles, powders, aerosols, and related methods.

In some aspects, the compositions and methods of the present invention exclude alanine, exclude isoleucine, exclude leucine, exclude methionine, exclude phenylalanine, exclude proline, exclude tryptophan, or exclude valine. In other aspects, what is excluded are each of these amino acids, or any combination of these amino acids, where trace amounts are permitted, and what is excluded are amino acids at levels that are pharmaceutically active, or where what is excluded are amino acids at levels that are at a sufficient concentration to have buffering capacity. Moreover, in some aspects what is excluded is aminoglycosides. Also, what can be excluded is water-soluble polypeptides.

Pharmaceutically Acceptable Compounds

The dispersible powders of the invention can comprise one or more pharmaceutically acceptable compounds or molecules. It is believed that any pharmaceutically-acceptable compound or molecule having the suitable solubility, etc., can be incorporated into the dispersible powders described herein. In some embodiments, the pharmaceutically acceptable compound(s) is capable of ameliorating an ailment of the lung. Exemplary lung ailments include but are not limited to microbial or viral infections or lung cancer. As shown in the Examples, a variety of molecules can be incorporated into the dispersible powders of the invention while maintaining production of a high percentage of smaller particles.

In some embodiments, the pharmaceutically acceptable compound is gallium (including but not limited to a salt thereof). The dispersible powders can comprise, for example, a therapeutically effective dose of gallium in the form of a pharmaceutically acceptable salt or complex, wherein said composition is suitable for delivery to the lung or deep lung by inhalation and comprising from about 1% by weight to about 90% by weight gallium. In some embodiments, the salt is a counterion selected from the group consisting of nitrate, citrate, chloride, or a mixture thereof. In some embodiments, the composition further comprises a complexing agent, which for example, can be selected from the group consisting of mannitol, maltolate or a derivative, protoporphyrin IX or a derivative, lactoferrin, transferrin, ferritin, bacterial siderophores belonging to the catecholate, hydroxamate, and hydroxycarboxylate groups, bacterial hemophores, and any chelators of iron.

In certain embodiments, the gallium composition may also include other excipients, in addition to the amino acid, such as proteins, surfactants, and polymers. Exemplary proteins are human serum albumin and recombinant human serum albumin. Surfactants can be chosen from a group consisting of polyethylene, polypropylene glycol, polyethylene glycol sorbitan monolaurate, or polyoxyethylene sortiban monooleate. Examples of polymers, selected from both biopolymers and synthetic polymers, include alginic acid, alginates, heparin, heparin sulfates, hyaluronic acid, hyaluronates, chitosan, chitin, starch, starch derivatives, carboxymethyl starch, hydroxyethyl starch (HES), dextran, polyvinyl pyrrolidone (PVP), gelatin, collagen, chrondroitin sulfate, or polyvinyl alcohol.

In some embodiments, gallium (III) is provided in the form of a pharmaceutically acceptable salt, comprising from about 1% by weight to about 90% by weight gallium (III) wherein the pharmaceutically acceptable salt is nitrate, citrate, chloride, or a mixture thereof. In some embodiments, the pharmaceutically acceptable compound comprises a salt of gallium (III) and a counterion, comprising from about 1% by weight to about 90% by weight gallium (III), from about 5% to about 90%, from about 10% to about 90%, from about 20% to about 90%, from about 40% to about 90%, from about 60% to about 90%, or from about 80% to about 90%, by weight gallium (III). High concentrations of gallium salts, such as gallium citrate, may be relatively insoluble, or may be substantially insoluble. In some embodiments, the concentration of gallium (III) is less than 1000 mM, less than 800 mM, less than 600 mM, less than 400 mM, less than 200 mM, less than 150 mM, less than 125 mM, less than 100 mM, less than 80 mM, less than 60 mM, less than 40 mM, or less than 20 mM.

In some embodiments, the pharmaceutically-acceptable molecule is a vaccine. Vaccines can comprise, for example, subunit-protein based antigen, with and without adjuvant, and can optionally include aluminum, inactivated viruses, toxoids, and live attenuated viruses and bacteria. The powder can further include one or a mixture of hydrophobic amino acids as described herein, optionally with any one of the following, but not limited to, salts, peptides, oligonucleotides, proteins, and vaccines.

Methods of Making Powders

Droplets of suspensions or solutions can be dried to form particles. The drying can be conducted by any means appropriate to the droplet composition and intended use. For example, the droplets can be sprayed into a stream of drying gas, onto a drying surface, into a cold fluid to freeze the droplets for later lyophilization, and the like. Dry particles can have moisture content (e.g., residual moisture), for example, of less than 15%, less than 10%, less than 5%, less than 3%, less than 1.5% or about 1%.

In one embodiment, the droplets are sprayed into a stream of a drying gas. For example, the drying gas can be an inert gas, such as nitrogen, at a temperature ranging from ambient temperatures to 200° C. In many cases, the stream of drying gas can enter the drying chamber to contact the droplets at a temperature of 150° C. or less, 100° C., 70° C., 50° C., 30° C. or less. The particles can be collected by settling, filtration, impact, etc. Particles can be exposed to secondary drying conditions to remove additional moisture.

The dry powder particles produced by spray drying can be room temperature stable and exhibit appropriate powder properties for deep lung delivery as well as for fabrication into other dosage formats such as oral wafers, oral thin films, capsules, tablets, etc.

Alternately, the droplets can be lyophilized to dryness. In one embodiment, the droplets are sprayed into liquid nitrogen to form frozen droplets. The droplets can settle out of the liquid nitrogen, or be removed by filtration or evaporation of the nitrogen. The collected frozen droplets can be placed in a vacuum chamber and lyophilized to form dry particles, e.g., without ever exposing the bioactive materials to high temperatures.

Aerosols, propellants, inhalers, methods for deriving a dry powder from a solution, relevant formulations, are available. See, e.g., Hickey, A. J. (2003) Pharmaceutical Inhalation Aerosol Technology, 2nd ed., (Drugs and the Pharmaceutical Sciences) Informa Healthcare; Zeng, X. M., Martin, G. P., Marriott, C. (2000) Particulate Interactions in Dry Powder Formulation for Inhalation (Pharmaceutical Science Series) Informa Healthcare; and Gradon, L., Marijnissen, J. C. (2003) Optimization of Aerosol Drug Delivery, Springer.

Alternatively, dry powder particles can be produced by spray freeze drying, in which the pharmaceutical substances are dissolved in a solution, or prepared as a suspension, and then sprayed through an atomizing nozzle into a cold gas phase, typically liquid nitrogen, resulting in frozen particles, which are then freeze dried. See, e.g., U.S. Pat. No. 7,007,406 issued to Wang and Finlay, Mumenthaler and Leuenberger (1991) Atmospheric spray-freeze drying: a suitable alternative in freeze-drying technology. Int J Pharm 72:97-110, Leuenberger (2002) Spray freeze-drying—The process of choice for low water soluble drugs? J Nano Res 4:111-119, van Drooge, Hinrichs, et al. (2005) Spray freeze drying to produce a stable $\Delta^9$-tetrahydrocannabinol containing inulin-based solid dispersion powder suitable for inhalation. Eur J Pharm Sci 26:231-240. Similarly to spray drying, the aerosol properties of dry powders produced by spray freeze drying can be enhanced by incorporating a hydrophobic amino acid to the initial solution.

Other modes of dry powder production can be achieved through fluidized bed drying (see, e.g., U.S. Pat. No. 4,624,058 issued to Nakayasu, et al, Chandran, et al (1990) Fluidized bed drying of solids AICHE J 36:29-38, Frake, et al (1997) Process control and end-point determination of a fluid bed granulation by application of near infra-red spectroscopy. Int J Pharm 151:75-80), supercritical fluid assisted drying (see, e.g., Sellers, et al. Dry powders of stable protein formulations from aqueous solutions prepared using supercritical $CO_2$-assisted aerosolization. J Pharm Sci 90:785-797, Jovanovic, et al. Stabilization of proteins in dry powder formulations using supercritical fluid technology. Pharm Res 21:1955-1969, Fages, et al. (2004) Particle generation for pharmaceutical applications using supercritical fluid technology. Powder Tech 141:219-226), and spray coating (see, e.g., U.S. Pat. No. 4,117,801 issued to Dannelly and Leonard, U.S. Pat. No. 4,302,481 issued to Ribmitz, et al., U.S. Pat. No. 4,302,440 issued to John, et al.), to name a few. Utilizing any of these methods, the aerosol properties of dry powders can be enhanced by incorporating a hydrophobic amino acid to the initial solution.

EXAMPLES

The following examples are offered to illustrate, but not to limit the scope of the claimed invention.

Example 1

The Use of Hydropathy Index to Engineer Dispersible Powders of Gallium-Citrate Sodium citrate dihydrate was dissolved in nano-pure water to obtain 1.5% (w/v) sodium citrate. To the solution, Ga$(NO_3)_3 \cdot 9H_2O$ was dissolved to obtain 1.5% (w/v) Ga$(NO_3)_3$. In addition, amino acids of varying hydropathy index were added to the solution and the pH was adjusted to 7.0 (Table 1). The concentration of the amino acid in the solution was 0.8% (w/v) in all cases.

The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder is indicated in Table 1.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders are shown in Table 1. The correlation of $FPD_{<3.3\ \mu m}$ to the hydropathy index of the amino acids is shown in FIG. 1.

TABLE 1

| Amino Acid | Hydropathy Index | Residual Moisture (%, w/w) | $FPD_{<3.3\ \mu m}$ (%) | $FPD_{<4.7\ \mu m}$ (%) | MMAD (μm) |
|---|---|---|---|---|---|
| Isoleucine | 4.5 | 5.74 ± 0.55 | 26.3 | 49.9 | 5.10 ± 0.28 |
| Valine | 4.2 | 5.02 ± 0.49 | 35.5 | 57.5 | 4.35 ± 0.07 |
| Leucine | 3.8 | 5.9 ± 0.03 | 62.0 | 78.7 | 2.60 ± 0.00 |
| Phenylalanine | 2.8 | 4.55 ± 0.86 | 36.1 | 54.7 | 4.50 ± 0.14 |
| Glycine | −0.4 | 5.34 ± 1.80 | 3.7 | 17.5 | >9 |
| Tryptophan | −0.9 | 6.36 ± 0.78 | 30.7 | 55.2 | 4.60 ± 0.14 |
| Histidine | −3.2 | 4.53 ± 0.37 | 31.0 | 52.4 | 4.75 ± 0.07 |
| Glutamic Acid | −3.5 | 4.85 ± 0.03 | 26.3 | 39.7 | 6.50 ± 0.99 |
| Arginine | −4.5 | 5.30 ± 0.32 | 17.9 | 32.8 | 7.15 ± 0.92 |

Example 2

The Use of $\Delta G_{water-vapor}$ Index to Engineer Dispersible Powders of Gallium-Citrate Sodium citrate dihydrate was dissolved in nano-pure water to obtain 1.5% (w/v) sodium citrate. To the solution, Ga$(NO_3)_3 \cdot 9H_2O$ was dissolved to obtain 1.5% (w/v) Ga$(NO_3)_3$. In addition, amino acids of varying $\Delta G_{water-vapor}$ index were added to the solution and the pH was adjusted to 7.0 (Table 2). The concentration of the amino acid in the solution was 0.8% (w/v) in all cases.

The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder is indicated in Table 2.

Figure 2:
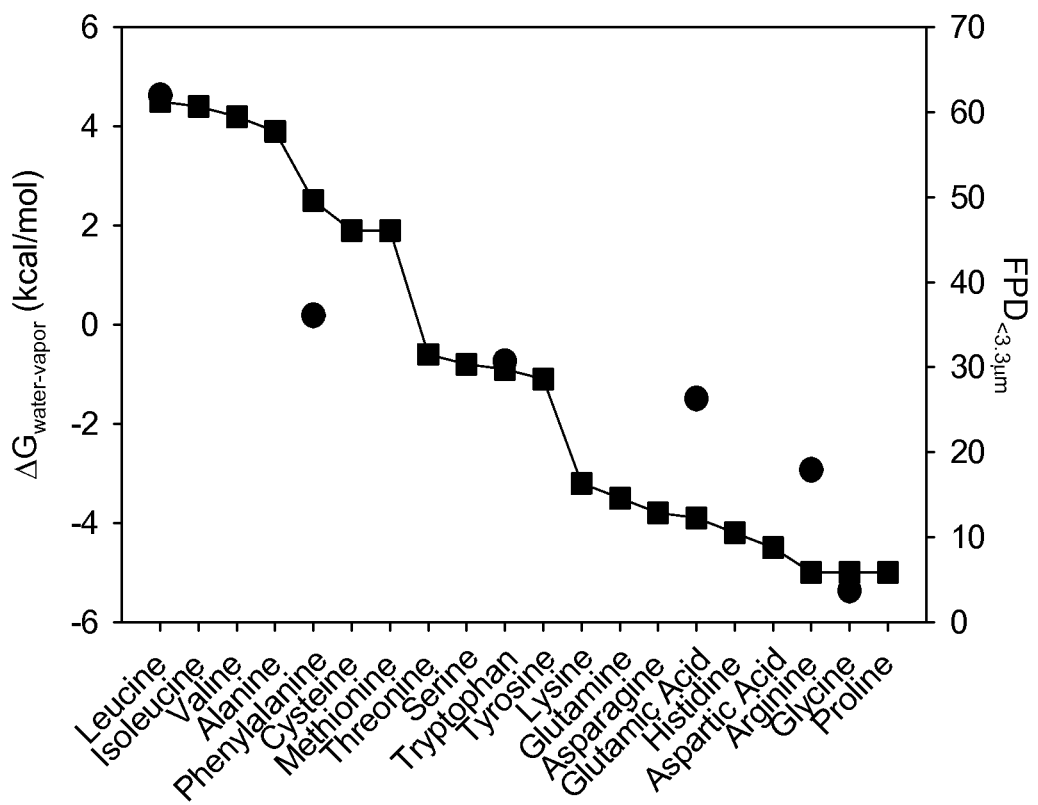
FIG. 2 shows the correlation between the water-to-vapor transfer free energy (■), $\Delta G_{water-vapor}$, of the amino acids to the $FPD_{<3.3 \mu m}$ (●) of the spray dried powders containing gallium-citrate.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders are shown in Table 2. The correlation of $FPD_{<3.3\ \mu m}$ to the $\Delta G_{water\text{-}vapor}$ index of the amino acids is shown in FIG. 2.

TABLE 2

| Amino Acid | $\Delta G_{water\text{-}vapor}$ | Residual Moisture (%, w/w) | $FPD_{<3.3\ \mu m}$ (%) | $FPD_{<4.7\ \mu m}$ (%) | MMAD (μm) |
|---|---|---|---|---|---|
| Leucine | 4.5 | 5.9 ± 0.03 | 62.0 | 78.7 | 2.60 ± 0.00 |
| Isoleucine | 4.4 | 5.74 ± 0.55 | 26.3 | 49.9 | 5.10 ± 0.28 |
| Valine | 4.2 | 5.02 ± 0.49 | 35.5 | 57.5 | 4.35 ± 0.07 |
| Phenylalanine | 2.5 | 4.55 ± 0.86 | 36.1 | 54.7 | 4.50 ± 0.14 |
| Tryptophan | −0.9 | 6.36 ± 0.78 | 30.7 | 55.2 | 4.60 ± 0.14 |
| Glutamic Acid | −3.9 | 4.85 ± 0.03 | 26.3 | 39.7 | 6.50 ± 0.99 |
| Histidine | −4.2 | 4.53 ± 0.37 | 31.0 | 52.4 | 4.75 ± 0.07 |
| Arginine | <−5 | 5.30 ± 0.32 | 17.9 | 32.8 | 7.15 ± 0.92 |
| Glycine | <−5 | 5.34 ± 1.80 | 3.7 | 17.5 | >9 |

Example 3

The Use of Protein to Engineer Dispersible Powders of Gallium-Citrate

Sodium citrate dihydrate was dissolved in nano-pure water to obtain 1.5% (w/v) sodium citrate. To the solution, Ga(NO$_3$)$_3$.9H$_2$O was dissolved to obtain 1.5% (w/v) Ga(NO$_3$)$_3$. In addition, 1 wt % of human serum albumin (HSA) was added to the solution and the pH was adjusted to 7.0.

The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder was 13.1±4.6%.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders were 30.6%, 49.8%, and 5.00±0.00 μm, respectively.

Example 4

The Use of Surfactant to Engineer Dispersible Powders of Gallium-Citrate

Sodium citrate dihydrate was dissolved in nano-pure water to obtain 1.5% (w/v) sodium citrate. To the solution, Ga(NO$_3$)$_3$.9H$_2$O was dissolved to obtain 1.5% (w/v) Ga(NO$_3$)$_3$. In addition, 0.1 wt % of Pluronic F68 was added to the solution and the pH was adjusted to 7.0.

The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder was 12.1±0.4%.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders were 11.2%, 19.3%, and >9 μm, respectively.

Example 5

The Use of Polymer to Engineer Dispersible Powders of Gallium-Citrate

Sodium citrate dihydrate was dissolved in nano-pure water to obtain 1.5% (w/v) sodium citrate. To the solution, Ga(NO$_3$)$_3$.9H$_2$O was dissolved to obtain 1.5% (w/v) Ga(NO$_3$)$_3$. In addition, 0.1 wt % of PEG was added to the solution and the pH was adjusted to 7.0.

The solution was spray dried at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder was 10.8±3.2%.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders were 5.7%, 10.5%, and >9 μm, respectively.

Example 6

The Use of Hydropathy Index and Delta G to Engineer Dispersible Powders of Gallium-Citrate Sodium citrate dihydrate was dissolved in nano-pure water to obtain 3.0% (w/v) sodium citrate. To the solution, Ga(NO$_3$)$_3$.9H$_2$O was dissolved to obtain 1.5% (w/v) Ga(NO$_3$)$_3$. In addition, amino acids of varying hydropathy index were added to the solution and the pH was adjusted to 7.0, unless otherwise indicated (Table 3 and Table 3.5). The concentration of the amino acid in the solution was 1.2% (w/v) in all cases.

The solution was spray dried in a Büchi B-190 at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder is indicated in Table 3 and Table 3.5.

Figure 3:
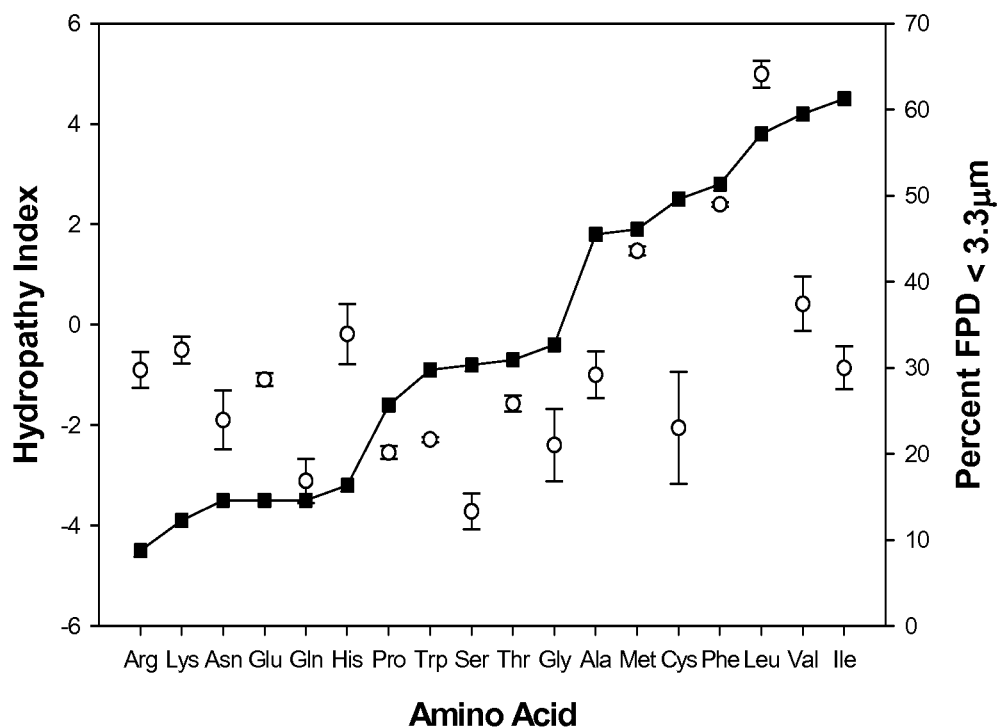
FIG. 3 shows the correlation between the hydropathy index (■) of the amino acids to the $FPD_{<3.3 \mu m}$ (○) of the spray dried powders containing gallium-citrate. All solutions formulations had a final pH of 7.0, except for the cysteine formulation which had a final pH of 2.8.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders are shown in Table 3 and Table 3.5. The correlation of $FPD_{<3.3\ \mu m}$ to the hydropathy index of the amino acids is shown in FIG. 3. The correlation of $FPD_{<3.3\ \mu m}$ to the delta G evaporation of the amino acids is shown in FIG. 3.5.

TABLE 3

| Amino Acid | Hydropathy Index | Residual Moisture (%, w/w) | $FPD_{<3.3 \mu m}$ (%) | $FPD_{<4.7 \mu m}$ (%) | MMAD (μm) |
|---|---|---|---|---|---|
| Isoleucine | 4.5 | 5.54 ± 0.72 | 30.0 ± 2.5 | 56.8 ± 3.1 | 4.51 ± 0.22 |
| Valine | 4.2 | 4.83 ± 0.13 | 37.4 ± 3.2 | 54.5 ± 3.0 | 4.06 ± 0.23 |
| Leucine | 3.8 | 5.17 ± 0.37 | 64.1 ± 1.6 | 84.3 ± 1.6 | 2.67 ± 0.05 |
| Phenylalanine | 2.8 | 6.09 | 49.0 ± 0.2 | 71.2 ± 0.2 | 3.36 ± 0.02 |
| Cysteine[1] | 2.5 | 4.74 ± 0.37 | 23.0 ± 6.5 | 47.4 ± 3.9 | 5.25 ± 0.38 |
| Methionine | 1.9 | 5.79 ± 0.47 | 43.6 ± 0.5 | 64.4 ± 1.0 | 3.75 ± 0.05 |
| Alanine | 1.8 | 5.57 ± 0.17 | 29.2 ± 2.7 | 51.8 | 4.86 ± 0.05 |
| Glycine | −0.4 | 4.32 ± 0.43 | 21.0 ± 4.2 | 40.2 ± 2.1 | 6.06 ± 0.27 |
| Threonine | −0.7 | 4.70 ± 0.12 | 25.8 ± 1.0 | 51.6 ± 0.4 | 4.87 ± 0.04 |
| Serine | −0.8 | 5.46 ± 0.61 | 13.3 ± 2.1 | 27.8 ± 2.9 | 8.41 ± 0.97 |
| Tryptophan | −0.9 | 4.96 ± 0.46 | 21.7 ± 0.3 | 46.8 ± 0.8 | 5.26 ± 0.07 |
| Tyrosine | −1.3 | N/A | N/A | N/A | N/A |
| Proline | −1.6 | 4.56 ± 0.10 | 20.2 ± 0.7 | 43.9 ± 0.7 | 5.48 ± 0.12 |
| Histidine | −3.2 | 5.51 ± 0.78 | 33.9 ± 3.5 | 54.5 ± 3.0 | 4.61 ± 0.28 |
| Glutamate | −3.5 | 4.56 ± 0.10 | 28.6 ± 0.8 | 49.1 ± 0.6 | 5.09 ± 0.07 |
| Glutamine | −3.5 | 6.26 ± 0.35 | 16.9 ± 2.6 | 34.9 ± 4.4 | 6.57 ± 0.60 |
| Aspartic Acid | −3.5 | N/A | N/A | N/A | N/A |
| Asparagine | −3.5 | 5.28 ± 0.31 | 23.9 ± 3.4 | 46.4 ± 2.8 | 5.36 ± 0.29 |
| Lysine | −3.9 | 5.24 ± 0.4 | 32.1 ± 1.6 | 51.6 ± 1.5 | 4.84 ± 0.16 |
| Arginine | −4.5 | 4.55 ± 0.29 | 29.7 ± 2.1 | 45.7 ± 4.4 | 5.65 ± 0.75 |

[1] pH = 2.78

TABLE 3.5

| Amino Acid | Delta G water-vapor (kcal/mol) | Residual Moisture (%, w/w) | $FPD_{<3.3 \mu m}$ (%) | $FPD_{<4.7 \mu m}$ (%) | MMAD (μm) |
|---|---|---|---|---|---|
| Leucine | 4.5 | 5.17 ± 0.37 | 64.1 ± 1.6 | 84.3 ± 1.6 | 2.67 ± 0.05 |
| Isoleucine | 4.4 | 5.54 ± 0.72 | 30.0 ± 2.5 | 56.8 ± 3.1 | 4.51 ± 0.22 |
| Valine | 4.2 | 4.83 ± 0.13 | 37.4 ± 3.2 | 54.5 ± 3.0 | 4.06 ± 0.23 |
| Alanine | 3.9 | 5.57 ± 0.17 | 29.2 ± 2.7 | 51.8 | 4.86 ± 0.05 |
| Phenylalanine | 2.5 | 6.09 | 49.0 ± 0.2 | 71.2 ± 0.2 | 3.36 ± 0.02 |
| Cysteine[1] | 1.9 | 4.74 ± 0.37 | 23.0 ± 6.5 | 47.4 ± 3.9 | 5.25 ± 0.38 |
| Methionine | 1.9 | 5.79 ± 0.47 | 43.6 ± 0.5 | 64.4 ± 1.0 | 3.75 ± 0.05 |
| Threonine | −0.6 | 4.70 ± 0.12 | 25.8 ± 1.0 | 51.6 ± 0.4 | 4.87 ± 0.04 |
| Serine | −0.8 | 5.46 ± 0.61 | 13.3 ± 2.1 | 27.8 ± 2.9 | 8.41 ± 0.97 |
| Tryptophan | −0.9 | 4.96 ± 0.46 | 21.7 ± 0.3 | 46.8 ± 0.8 | 5.26 ± 0.07 |
| Lysine | −3.2 | 5.24 ± 0.4 | 32.1 ± 1.6 | 51.6 ± 1.5 | 4.84 ± 0.16 |
| Glutamine | −3.5 | 6.26 ± 0.35 | 16.9 ± 2.6 | 34.9 ± 4.4 | 6.57 ± 0.60 |
| Asparagine | −3.8 | 5.28 ± 0.31 | 23.9 ± 3.4 | 46.4 ± 2.8 | 5.36 ± 0.29 |
| Glutamate | −3.9 | 4.56 ± 0.10 | 28.6 ± 0.8 | 49.1 ± 0.6 | 5.09 ± 0.07 |
| Histidine | −4.2 | 5.51 ± 0.78 | 33.9 ± 3.5 | 54.5 ± 3.0 | 4.61 ± 0.28 |
| Arginine | N/A | 4.55 ± 0.29 | 29.7 ± 2.1 | 45.7 ± 4.4 | 5.65 ± 0.75 |
| Glycine | N/A | 4.32 ± 0.43 | 21.0 ± 4.2 | 40.2 ± 2.1 | 6.06 ± 0.27 |
| Proline | N/A | 4.56 ± 0.10 | 20.2 ± 0.7 | 43.9 ± 0.7 | 5.48 ± 0.12 |

[1] pH = 2.78

Example 7

The Use of Different Excipients at Different Weight/Volume Ratios to Engineer Dispersible Powders of Gallium-Citrate Sodium citrate dihydrate was dissolved in nano-pure water to obtain 3.0% (w/v) sodium citrate. To the solution, Ga(NO$_3$)$_3$·9H$_2$O was dissolved to obtain 1.5% (w/v) Ga(NO$_3$)$_3$. In addition, Leucine, Glutamate, Phenylalanine, or Alanine was added to the solution and the pH was adjusted to 7.0. The concentration of the amino acid in the solution ranged between 0.2% and 2.0% (w/v). The residual moisture content of the resulting powder is indicated in Table 4.

The solution was spray dried in a Büchi B-190 at $T_{in}/T_{out}$=80/60° C., q=0.5 mL/min, and $P_{atm}$=15 psi. The powder was collected under controlled temperature and humidity of 30° C. and <5% RH, respectively.

Figure 4:
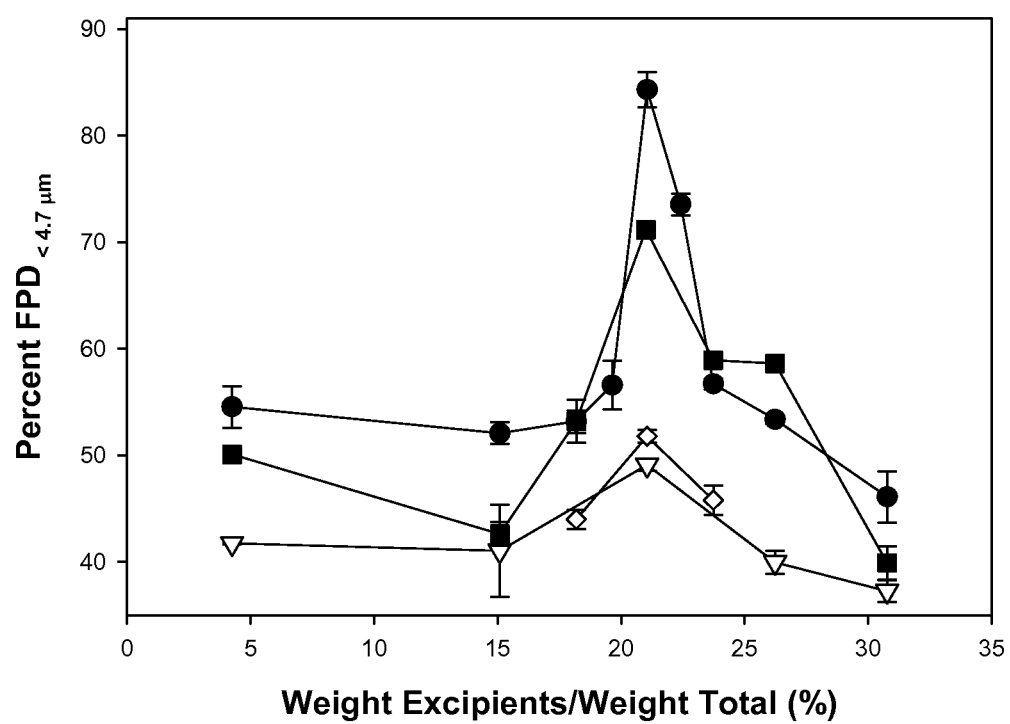
FIG. 4 compares the $FPD_{<4.7 \mu m}$ of gallium-citrate spray dried powders containing leucine (●), alanine (◇), glutamate (∇), and phenylalanine (■) at different weight ratios.
Figure 5:
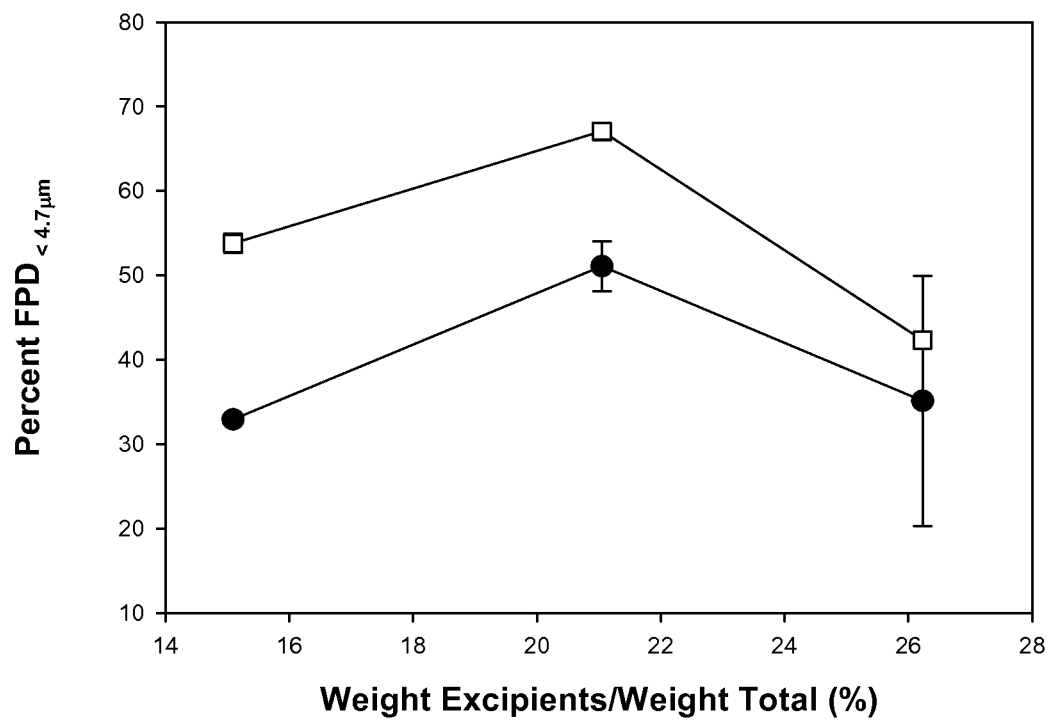
FIG. 5 shows the percent $FPD_{4.7 \mu m}$ of leucine combined with either glucose (●) or raffinose (□) at different weight excipients to weight total ratios.
Figure 6:
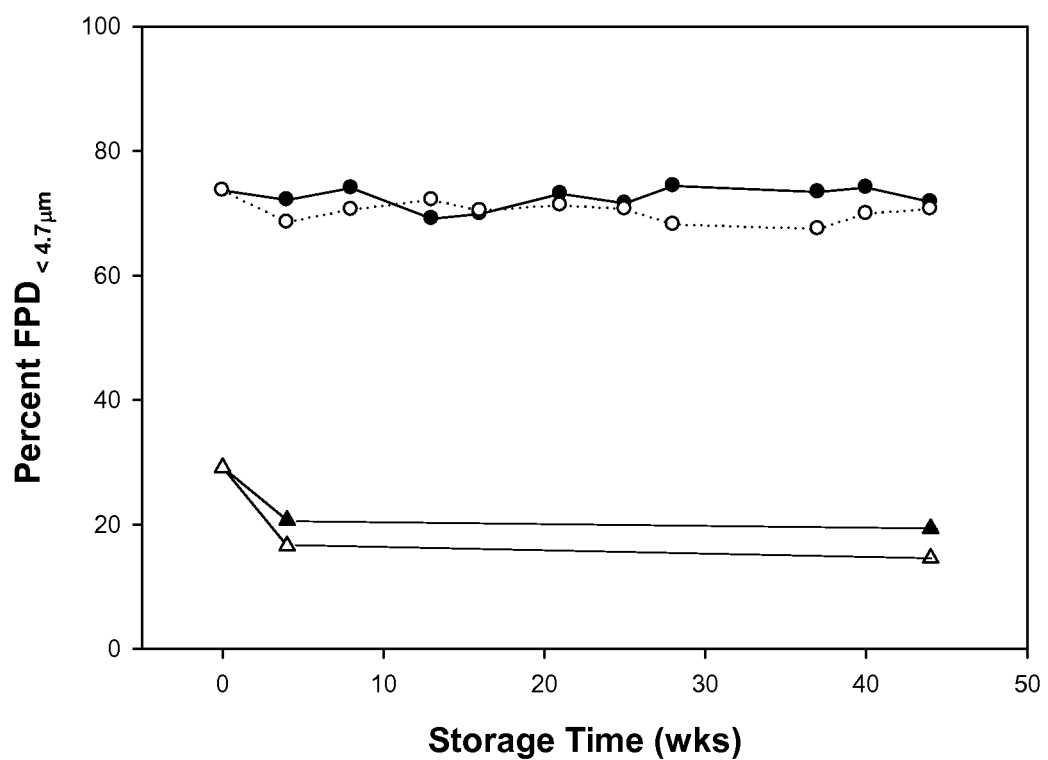
FIG. 6 compares the $FPD_{<4.7 \mu m}$ of gallium-citrate stored at 4° C. (▲), gallium-citrate stored at 37° C. (Δ), gallium-citrate-leucine stored at 4° C. (●), and gallium-citrate-leucine stored at 37° C. (○) over a 44-week period.

50 mg of the powder was encapsulated inside of a type 2 capsule and tested for particle size distribution using an Anderson cascade impactor (ACI) fitted with Turbospin® under a flow rate of 28 L/min. $FPD_{<3.3 \mu m}$, $FPD_{<4.7 \mu m}$, and MMAD of the spray dried powders were calculated and are presented in Table 4. The relation between $FPD_{<4.7 \mu m}$ to the weight percent of the amino acids is shown in FIG. 4.

TABLE 4

| Amino Acid | % w/v | Residual Moisture (%, w/w) | FPD$_{<3.3 \mu m}$ (%) | FPD$_{<4.7 \mu m}$ (%) | MMAD (μm) |
|---|---|---|---|---|---|
| Glu | 0.20% | 7.71 ± 0.26 | 19.43 ± 1.485 | 41.75 ± 0.082 | 5.76 ± 0.08 |
| Glu | 0.80% | 6.02 ± 0.17 | 19.07 ± 4.5 | 41.01 ± 4.335 | 5.74 ± 0.38 |
| Glu | 1.20% | 5.46 ± 0.21 | 28.62 ± 0.757 | 49.1 ± 0.554 | 5.09 ± 0.07 |
| Glu | 1.60% | 5.48 ± 0.24 | 17.96 ± 1.456 | 39.97 ± 1.07 | 5.86 ± 0.12 |
| Glu | 2.00% | 7.15 ± 0.83 | 17.69 ± 0.318 | 37.26 ± 1.02 | 6.16 ± 0.10 |
| Leu | 0.20% | 5.64 ± 0.19 | 31.08 ± 2.496 | 54.46 ± 1.956 | 4.64 ± 0.17 |
| Leu | 0.80% | 5.50 ± 0.33 | 26.10 ± 3.54 | 52.08 ± 1.02 | 4.84 ± 0.08 |
| Leu | 1.00% | 7.07 ± 0.08 | 29.18 ± 1.711 | 53.22 ± 2.04 | 4.74 ± 0.17 |
| Leu | 1.10% | 5.75 ± 0.22 | 27.3 ± 3.6 | 56.6 ± 2.3 | 4.54 ± 0.16 |
| Leu | 1.20% | 5.17 ± 0.37 | 64.11 ± 1.57 | 84.32 ± 1.627 | 2.67 ± 0.05 |
| Leu | 1.30% | 2.87 ± 0.52 | 46.5 ± 1.4 | 73.55 ± 1.02 | 3.46 ± 0.05 |
| Leu | 1.40% | 4.05 ± 0.66 | 30.3 ± 1.31 | 56.7 ± 0.51 | 4.53 ± 0.04 |
| Leu | 1.60% | 6.04 ± 0.16 | 27.58 ± 0.050 | 53.37 ± 0.418 | 4.73 ± 0.04 |
| Leu | 2.00% | 4.60 ± 0.43 | 22.75 ± 1.65 | 46.12 ± 2.403 | 5.33 ± 0.21 |
| Phe | 0.20% | 7.10 ± 0.60 | 27.22 ± 1.44 | 50.1 ± 0.81 | 4.99 ± 0.07 |
| Phe | 0.80% | 5.17 ± 0.26 | 20.03 ± 2.19 | 42.63 ± 1.102 | 5.55 ± 0.10 |
| Phe | 1.00% | 5.17 ± 0.26 | 27.71 ± 1.506 | 53.18 ± 1.049 | 4.77 ± 0.08 |
| Phe | 1.20% | 6.09 | 48.97 ± 0.247 | 71.19 ± 0.237 | 3.36 ± 0.02 |
| Phe | 1.40% | 2.73 ± 0.60 | 32.02 ± 0.035 | 58.93 ± 0.325 | 4.38 ± 0.03 |
| Phe | 1.60% | 4.15 ± 0.97 | 33.54 ± 1.434 | 58.63 ± 0.688 | 4.37 ± 0.07 |
| Phe | 2.00% | 5.45 ± 0.95 | 20.3 ± 1.64 | 39.9 ± 1.56 | 6.01 ± 0.10 |
| Ala | 1.00% | 4.74 ± 0.50 | 20.46 ± 0.509 | 43.95 ± 0.858 | 5.50 ± 0.07 |
| Ala | 1.20% | 5.57 ± 0.17 | 29.17 ± 2.72 | 51.76 ± 0.646 | 4.86 ± 0.05 |
| Ala | 1.40% | 6.33 ± 0.35 | 21.13 ± 0.95 | 45.81 ± 1.35 | 5.35 ± 0.13 |

Example 8

The Use of Leucine with Sugars to Engineer Dispersible Powders

Raffinose pentahydrate or glucose monohydrate was dissolved in nano-pure water to obtain 4.5% (w/v) raffinose or glucose. To the solution, leucine was added and the pH was adjusted to 7.0. The concentration of the leucine in the solution ranged between 0.8% and 1.6% (w/v).

The solution was spray dried in a Büchi B-190 at $T_{in}/T_{out}$=80/60° C., q=0.5 mL/min, and $P_{atm}$=15 psi. The powder was collected under controlled temperature and humidity of 30° C. and <5% RH, respectively. The residual moisture content of the resulting powder is indicated in Table 5.

50 mg of the powder was encapsulated inside of a type 2 capsule and tested for particle size distribution using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders were calculated and are shown in Table 5. The relation between $FPD_{<4.7\ \mu m}$ to the weight percent of the amino acids is shown in FIG. 5.

TABLE 5

| Sugar | % Weight Leucine | Residual Moisture (%, w/w) | $FPD_{<3.3\ \mu m}$ (%) | $FPD_{<4.7\ \mu m}$ (%) | MMAD (μm) |
|---|---|---|---|---|---|
| Raffinose | 15.09 | 4.16 ± 0.05 | 29.0 ± 0.4 | 53.8 ± 1.1 | 4.70 ± 0.12 |
| Raffinose | 21.05 | 3.83 ± 0.22 | 42.5 ± 1.5 | 67.1 ± 1.0 | 3.73 ± 0.08 |
| Raffinose | 26.23 | | 19.8 ± 0.8 | 42.3 ± 4.0 | 5.66 ± 0.03 |
| Glucose | 15.09 | 2.54 ± 0.76 | 13.8 ± 0.3 | 32.9 ± 0.2 | 6.67 ± 0.01 |
| Glucose | 21.05 | 2.49 ± 0.43 | 21.6 ± 1.4 | 51.1 ± 3.0 | 4.92 ± 0.24 |
| Glucose | 26.23 | 2.84 ± 0.10 | 21.0 ± 7.1 | 35.1 ± 14.8 | 6.46 ± 1.48 |

Example 9

Long Term Stability Storage of Gallium-Citrate

Sodium citrate dihydrate was dissolved in nano-pure water to obtain 2.25% (w/v) sodium citrate. To the solution, $Ga(NO_3)_3.9H_2O$ was dissolved to obtain 1.5% (w/v) $Ga(NO_3)_3$. Leucine was added to one formulation at 1.2% (w/v), but not the other. The pH was adjusted to 7.0.

The solution was spray dried in a Büchi B-190 at $T_{in}/T_{out}$=80/60° C., q=0.5 mL/min, and $P_{atm}$=15 psi. The powder was collected under controlled temperature and humidity of 30° C. and <5% RH, respectively.

50 mg of powder was then aliquot into type 2 capsules. These capsules were put into mylar bags with desiccants and stored at 37° C. and 4° C. Every month, the particle size distribution of the encapsulated powders was tested using an Anderson cascade impactor (ACI) fitted with Turbospin® under a flow rate of 28 L/min. $FPD_{<3.3\ \mu m}$, $FPD_{<4.7\ \mu m}$, and MMAD of the spray dried powders were calculated, but only the $FPD_{<4.7\ \mu m}$, and MMAD are shown in Table 6 and Table 7. The relation between $FPD_{<4.7\ \mu m}$ and storage time is shown in FIG. 6.

TABLE 6

| Excipient | Time (wks) | 4° C. MMAD (μm) | 4° C. FPD$_{<4.7\,\mu m}$ (%) | 37° C. MMAD (μm) | 37° C. FPD$_{<4.7\,\mu m}$ (%) |
|---|---|---|---|---|---|
| Leucine | 0 | 3.28 | 73.657 | 3.28 | 73.65 |
| Leucine | 4 | 3.49 | 72.10 | 3.62 | 68.51 |
| Leucine | 8 | 3.39 | 74.00 | 3.41 | 70.55 |
| Leucine | 13 | 3.76 | 69.08 | 3.49 | 72.110 |
| Leucine | 16 | 3.63 | 69.86 | 3.58 | 70.38 |
| Leucine | 21 | 3.57 | 73.11 | 3.49 | 71.26 |
| Leucine | 25 | 3.56 | 71.57 | 3.55 | 70.64 |
| Leucine | 28 | 3.48 | 74.37 | 3.67 | 68.16 |
| Leucine | 37 | 3.42 | 73.38 | 3.62 | 67.43 |
| Leucine | 40 | 3.42 | 74.08 | 3.43 | 69.88 |
| Leucine | 44 | 3.45 | 71.79 | 3.434 | 70.63 |

TABLE 7

| Excipient | Time (wks) | 4° C. MMAD (μm) | 4° C. FPD$_{<4.7\,\mu m}$ (%) | 37° C. MMAD (μm) | 37° C. FPD$_{<4.7\,\mu m}$ (%) |
|---|---|---|---|---|---|
| None | 0 | N/A | 29.17 | N/A | 29.17 |
| None | 4 | N/A | 16.56 | N/A | 16.56 |
| None | 44 | N/A | 14.58 | N/A | 14.58 |

Although the foregoing invention has been described by way of descriptions, data, and examples, it will be apparent to those skilled in the art that various changes and modifications can be practiced without departing from the spirit of the invention. Therefore the foregoing descriptions, data, and examples should not be construed as limiting the scope of the invention. All patents and published patent applications, identified herein, are incorporated by reference.

What is claimed is:

1. A pharmaceutically acceptable dispersible powder, comprising gallium and a hydrophobic monomeric amino acid excipient that is more hydrophobic than alanine, according to the Kyte-Doolittle index, wherein the powder only contains amino acids in monomeric form,
wherein the mass of the excipient is 15%-25% of the mass of the powder, and
wherein the fine particle distribution (FPD) of the powder that is under 3.3 microns is greater than 30%, or wherein the mass median aerodynamic diameter (MMAD) of the powder is under 10 microns.

2. The pharmaceutically acceptable dispersible powder of claim 1, wherein the mass of the excipient is at least 20.5% the mass of the powder and 22% or less than the mass of the powder.

3. The pharmaceutically acceptable dispersible powder of claim 1, wherein the mass of the excipient is about 21% of the mass of the powder.

4. The pharmaceutically acceptable dispersible powder of claim 1, wherein the gallium is formulated as gallium citrate or gallium nitrate.

5. The pharmaceutically acceptable dispersible powder of claim 1, wherein the amino acid is leucine.

6. The pharmaceutically acceptable dispersible powder of claim 1, wherein the amino acid is selected from the group consisting of isoleucine, valine, phenylalanine, cysteine, and methionine.

7. The pharmaceutically acceptable dispersible powder of claim 1, made by a method comprising spray freeze-drying, fluidized bed drying, supercritical fluid assisted drying, or spray coating.

8. A pharmaceutically acceptable dispersible powder comprising a monomeric amino acid hydrophobic excipient, other than leucine, that is more hydrophobic than alanine, according to the Kyte-Doolittle index, wherein the powder only contains amino acids in monomeric form,
wherein the mass of the excipient is 15%-25% of the mass of the powder, and wherein the fine particle distribution (FPD) of the powder that is under 3.3 microns is greater than 30%, or wherein the mass median aerodynamic diameter (MMAD) of the powder is under 10 microns.

9. The pharmaceutically acceptable dispersible powder of claim 8, further comprising a pharmaceutically-active molecule.

10. The pharmaceutically acceptable dispersible powder of claim 9, wherein the pharmaceutically-active compound is gallium.

11. The pharmaceutically acceptable dispersible powder of claim 9, wherein the pharmaceutically-active compound is gallium citrate or gallium nitrate.

12. The pharmaceutically acceptable dispersible powder of claim 8, wherein the mass of the excipient is at least 20.5% the mass of the powder and 22% or less than the mass of the powder.

13. The pharmaceutically acceptable dispersible powder of claim 8, wherein the mass of the excipient is about 21% of the mass of the powder.

14. The pharmaceutically acceptable dispersible powder of claim 8, wherein the amino acid is selected from the group consisting of isoleucine, valine, phenylalanine, cysteine, and methionine.

15. The pharmaceutically acceptable dispersible powder of claim 8, made by a method comprising spray freeze-drying, fluidized bed drying, supercritical fluid assisted drying, or spray coating.

16. A pharmaceutically acceptable dispersible powder comprising monomeric leucine, wherein the mass of the leucine is at least 20.5% the mass of the powder and 22% or less than the mass of the powder, wherein the powder only contains amino acids in a monomeric form, and
wherein the fine particle distribution (FPD) of the powder that is under 3.3 microns is greater than 30%, or wherein the mass median aerodynamic diameter (MMAD) of the powder is under 10 microns.

* * * * *